United States Patent [19]

Petzoldt et al.

[11] 4,036,695
[45] July 19, 1977

[54] PROCESS FOR THE PREPARATION OF ESTRENE-3,17-DIONE DERIVATIVES

[75] Inventors: Karl Petzoldt; Rudolf Wiechert, both of Darmstadt, Germany

[73] Assignee: Schering Aktiengesellschaft, Berlin & Bergkamen, Germany

[21] Appl. No.: 633,415

[22] Filed: Nov. 19, 1975

[30] Foreign Application Priority Data

Nov. 23, 1974 Germany .............................. 2456068

[51] Int. Cl.$^2$ ............................................. C07B 29/02
[52] U.S. Cl. ................................. 195/51 B; 260/397.3
[58] Field of Search ..................... 195/51 B; 260/397.3

[56] References Cited

U.S. PATENT DOCUMENTS

| | | | |
|---|---|---|---|
| 3,214,448 | 10/1965 | Holmlund et al. | 195/51 B |
| 3,517,036 | 6/1970 | Diassi | 195/51 B |
| 3,749,742 | 7/1973 | Wiechert et al. | 260/397.3 |
| 3,939,187 | 2/1976 | Lehmann | 195/51 S |

*Primary Examiner* — Alvin E. Tanenholtz
*Attorney, Agent, or Firm* — Millen & White

[57] ABSTRACT

Estrene-3,17-diones of the formula

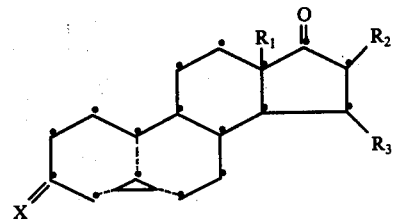

wherein X is oxo, or ketalized oxo, preferably alkylenedioxy of 2–6 carbon atoms or o-phenylenedioxy;

Δ is a carbon atom linked to the adjacent carbon atoms by a double bond and two single bonds;

$R_1$ is methyl or ethyl, and $R_2$ and $R_3$ collectively are a carbon-to-carbon bond or methylene, useful as intermediates for the production of pharmacologically active steroids, are prepared by fermenting 18-ethyl-4-estrene-3,17-dione or 18-methyl-4-estrene-3,17-dione with a fungal culture of the genus Penicillium or Fusarium to produce the corresponding 15α-hydroxy-steroid; in either order, converting the hydroxy group of the thus-produced 15α-hydroxy steroid to a sulfonic acid ester thereof and ketalizing the 3-keto group thereof; and treating the ketalized and esterified steroid with a base to form a Δ$^{15}$-compound or with dimethylsulfoxonium methylide to form a 15β,16β-methylene compound and, optionally, hydrolyzing the 3-ketal group.

11 Claims, No Drawings

PROCESS FOR THE PREPARATION OF ESTRENE-3,17-DIONE DERIVATIVES

BACKGROUND OF THE INVENTION

This invention relates to a process for the preparation of 15α-hydroxy, $\Delta^{15}$- and 15β,16β-methylene-estrene-3,17-diones and to novel intermediates thus-produced.

SUMMARY OF THE INVENTION

In a process aspect, this invention relates to a process which comprises hydroxylating a 4-estrene-3,17-dione of the formula

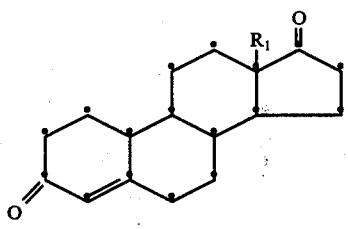

wherein $R_1$ is methyl or ethyl with a fungal culture of the genus Penicillium or Fusarium, to produce a 15α-hydroxy steroid of the formula

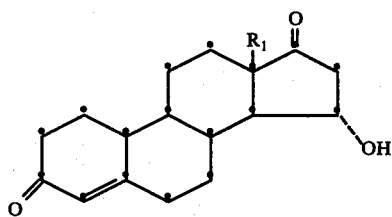

wherein $R_1$ is methyl or ethyl.

In a further process aspect, this invention relates to a method for the preparation of estren-17-ones of Formula I

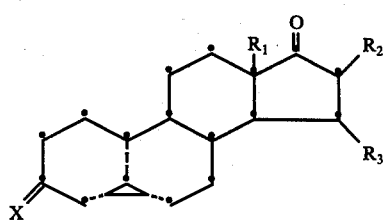

wherein X is oxo or ketalized oxo, preferably alkylenedioxy of 2–6 carbons, or o-phenylenedioxy;

$\Delta$ is a carbon atom linked to the adjacent carbon atoms by a double bond and two single bonds;

$R_1$ is methyl or ethyl; and $R_2$ and $R_3$ collectively are a carbon-to-carbon bond or methylene; which comprises a. fermenting an 18-alkyl-4-estrene-3,17-dione of Formula II with a fungal culture of the genus Penicillium or Fusarium to produce a 15α-hydroxy steroid of Formula III;

b. in either order, ketalizing the 3-keto group, preferably with an α- or β -alkanediol of 2-6 carbon atoms or with catechol, in the presence of an acidic catalyst, and acylating the 15α-hydroxy group to form a sulfonic acid ester thereof, preferably with a sulfonic acid chloride in the presence of a base, to produce an estrene-17-one of general Formula IV

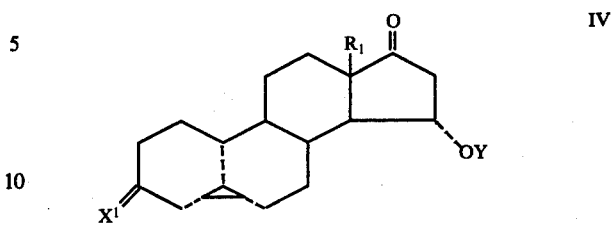

wherein $\Delta$ and $R_1$ are as in Formula I;

X is a ketalized oxo group, preferably of 2–6 carbon atoms and 2–3 carbon atoms bridging the oxygen atoms or o-phenylenedioxy; and Y is a sulfonyl group, preferably an alkylsulfonyl of 1–6 carbon atoms or arylsulfonyl of 6–10 carbon atoms; and c. either converting the ketalized and esterified steroid into a $\Delta^{15}$-steroid of general Formula I by treatment with a base or into a 15β,16β-methylene steroid of general Formula I by reaction with dimethyl sulfoxonium methylide; and optionally, hydrolyzing a ketal thus-obtained in a conventional manner into a corresponding 3-keto steroid of Formula I.

In a composition aspect, this invention relates to novel steroids of general Formula III and general Formula IV.

DETAILED DESCRIPTION

The estrene-3,17-dione derivatives of general Formula I are, as is known, pharmacologically active compounds and/or valuable intermediates for the preparation of pharmacologically effective steroids. In accordance with the processes known heretofore, estrene-3,17-diones can be produced only by very expensive, multistep syntheses such as those of DOS's [German offenlegungschriften] 1,593,500; 1,593,501; and 1,643,050, and J. Fried and J. A. Edwards: "Organic Reactions in Steroid Chemistry," van Nostrand-Reinhold Co., New York et al. [1972] 1:301 et seq.

In contrast thereto, the process of this invention provides estrene-3,17-dione derivatives of general Formula I by a simple route and in higher yields than obtained by conventional methods.

In the first step of the process of this invention, an 18-alkyl-4-estrene-3,17-dione of general Formula II is fermented with a fungal culture of the genus Penicillium or Fusarium.

Typical of suitable fungal strains for this fermentation are: Fusarium avenaceum (CBS 38662), Fusarium oxysporum (ATCC 7808 or ATCC 9991), Fusarium roseum (ATCC 14717), Penicillium canescens (ATCC 10419), Penicillium chrysogenum (ATCC 10003), Penicillium migricans (ATCC 9439), Penicillium stoloniferum (ATCC 14586), and Penicillium raistrickii (ATCC 10490). Penicillium raistrickii is particularly preferred.

The fermentation with these strains of fungi is conducted under conditions conventionally employed in the microbiological hydroxylation of steroids with fungal cultures.

Under the aforementioned conditions, the steroids of general Formula II are hydroxylated in surprisingly high yields to the 15α-hydroxy steroids of general Formula III. This advantageous result is highly unexpected because it is well known that Penicillia and Fusaria are capable hydroxylating steroids in the 6β- and 11α- as well as the 15α-position, and that these fungi also are capable of reducing keto steroids to the corresponding hydroxy steroids.

In the second and third steps of the process of this invention, the 15α-hydroxy steroids of general Formula III are ketalized, e.g., with an alkanediol or catechol, and acylated, e.g., with a sulfonic acid chloride. These steps are carried out in any desired sequence.

The selective ketalization is affected under the conditions customarily employed for the ketalization of 3-keto-Δ⁴-steroids. Thus, it is possible, for example, to react the steroids with an α or β-alkanediol of 2-6 carbon atoms, e.g., ethylene glycol, 1,3-propanediol, 2,3-butanediol, and 2,2-dimethylpropanediol, or with catechol or substituted catechols in an inert solvent, e.g., benzene, chloroform, methylene chloride, tetrachloroethane, diethyl ether, or tetrahydrofuran using an acidic catalyst, e.g., hydrogen chloride, sulfuric acid, perchloric acid, trifluoroacetic acid, p-toluenesulfonic acid. To improve the yields of the ketalization product, a drying agent is preferably added to the reaction mixture. Among preferred drying agents are calcium sulfate, magnesium sulfate and trialkyl formates.

A possible side-reaction during this ketalization is ketalization of the 17-keto group, especially if vigorous reaction conditions are used or the reaction time is long. To avoid this side-reaction, it is advantageous to determine the optimum reaction time in a preliminary experiment.

During the ketalization, the $\Delta^4$-double bond present in the steroid is isomerized into the $\Delta^{5(6)}$-position or the $\Delta^{5(10)}$-position. This isomerization does not affect the operability of the process of this invention, because, during the subsequent ketal cleavage reaction which is necessary for the preparation of pharmacologically active steroids, steroids having a 3-keto-Δ⁴-structure are again obtained.

The acylation of the 15α-hydroxy group with alkylsulfonyl chlorides or arylsulfonyl chlorides is done by the methods known for this purpose. Thus, the 15α-hydroxy steroids can be reacted, for example, with the sulfonyl chlorides, including alkylsulfonyl chlorides of 1-6 carbon atoms and arylsulfonyl chlorides of 6-10 carbon atoms. However, benzenesulfonyl chloride, p-toluenesulfonyl chloride, and methanesulfonyl chloride are preferred. The reaction is conducted in the presence of a tertiary amine, e.g., pyridine, lutidine, collidine, or 4-dimethylaminopyridine.

The thus-obtained compounds of general Formula IV can either be converted by treatment with bases into the $\Delta^{15}$-steroids of general Formula I, or they can be converted into the 15β,16β-methylene steroids of general Formula I be reaction with dimethyl sulfonium methylide.

The elimination of the sulfonic acid group is conducted in the presence of a base. Suitable bases include alkali metal hydroxides, alkaline earth metal hydroxides, alkali metal carbonates, alkali metal salts or lower carboxylic acids, and tertiary amines.

Examples of suitable bases are: sodium hydroxide, potassium hydroxide, calcium hydroxide, sodium carbonate, potassium carbonate, sodium acetate, potassium acetate, pyridine, lutidine and collidine. When tertiary amines are used for this reaction, these can simultaneously serve as the reaction solvent. When inorganic bases are used, the reaction is advantageously conducted in the presence of a dipolar aprotic solvent, e.g., dimethylformamide, N-methylacetamide, N-methylpyrrolidone, acetonitrile, dimethylsulfoxide or hexamethylphosphoric triamide.

During this elimination reaction, it is possible for the $\Delta^{15}$-double bond to isomerize to the $\Delta^{14}$-double bond, as is known from analogous eliminations. See J. Amer. Chem. Soc. 78 [1956]: 6347. To avoid this undesired reaction, the optimum reaction temperature and reaction time can be determined by preliminary experiments.

There is no danger of isomerization if the elimination reaction is conducted using an alkali metal salt of a lower carboxylic acid, e.g., of 2-6 carbon atoms, preferably sodium acetate or potassium acetate, in a dipolar aprotic solvent at a reaction temperature of $-20°$ to $+40°$ C. Surprisingly, under these conditions, the sulfonic acid ester residue is not exchanged for a carboxylic acid ester group, but instead is eliminated with the formation of a $\Delta^{15}$-double bond.

The compounds of general Formula IV can be converted into the 15β,16β-methylene steroids of general Formula I by reaction with dimethyl sulfoxonium methylide. This reaction can be conducted, for example, by reacting a trimethyl sulfonium halogenide in dimethyl sulfoxide with an equivalent amount of sodium hydride and then treating a compound of general Formula I with the thus-obtained dimethyl sulfoxonium methylide solution.

It has not heretofore been known that sulfonic acid esters of β-hydroxyketones are converted into cyclopropane derivatives under the above-described conditions.

If desired, the thus-obtained ketals can be hydrolyzed in a conventional manner by treatment with an aqueous acid. However, it is also possible to employ the ketals themselves as intermediates for the preparation of pharmacologically active steroids, as will be described in greater detail in the following example, -methylene-4-estren-3-one. as such example the synthesis of 17β-hydroxy-18-methyl-17α-ethynyl-15β,16β-methylene-4-estren-3-one. The corresponding 17β-hydroxy-17α-ethinyl-15β,16β-methylene-4-estren-3-one may be converted under the same conditions to the pharmacologically active 17β-hydroxy-17α-ethinyl-15β,16β-methylene-4-estrene-3-one.

Under the same conditions used for the convertion of the compounds of the general formula IV also the $\Delta^{15}$-compounds of the general formula I may be converted to the corresponding 15β,16β-methylene steroides.

Without further elaboration, it is believed that one silled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. A two-liter Erlenmeyer flask containing 500 ml. of a nutrient solution, autoclave-sterilized for 30 min. at 120° C., of 3.0% glucose, 1.0% corn steep, 0.2% NaNO₃, 0.1% KH₂PO₄, 0.2% K₂HPO₄, 0.05% MgSO₄, 0.002% FeSO₄, and 0.05% KCl is inoculated with a lyophilized culture of Penicillium raistrickii (ATCC 10490) and incubated on a rotary shaker for 72 hours at 30° C. With 250 ml. of this subculture, a 20-liter glass fermentor is then inoculated; this fermentor had previously been filled with 15 liters of a medium having the same composition, sterilized at 121° C. and under 1.1 atmospheres gauge. With the addition of "Silicone SH" as the defrother, the culture is grown at 29° C. for 24 hours under aeration (10 liters per minute), a pressure of 0.7 atmosphere gauge, and agitation (220 r.p.m.).

1.8 liters of the culture broth is transferred under sterile conditions into 26 liters of a nutrient medium having the same composition as the incubating medium, sterilized as described above, and grown under the same conditions as the preliminary fermentor culture. After 12 hours, 2 liters of a sterilized suspension of 120 g. of nat. 18-methyl-4-estrene-3,17-dione in distilled water, ground extremely fine in the presence of aqueous "Tween 80," is added and the mixture is further fermented.

The progression of the conversion is followed by analysis of the methyl isobutyl ketone extracts of fermentor samples by thin-layer chromatography. After an incubation time of about 70 hours, the conversion is complete. The fungus mycelium is now filtered off, and the culture broth is extracted twice with 20 liters of methyl isobutyl ketone. At the same time, the filtered-off mycelium is stirred intensively several times with a methyl isobutyl ketone, acetone, and water mixture and then extracted until no steroid substance is detectable.

The organic extract solutions are combined and evaporated to dryness under vacuum at a bath temperature of 50° C. The brown-crystalline residue is washed several times with hexane to remove the silicone oil, dried, and finally recrystallized from ethyl acetate after treatment with active charcoal to yield 97.3 g (76.5% of theory) of pure nat. 15α-hydroxy-18-methyl-4-estrene-3,17-dione, m.p. 175°-177° C.

b. 32 g. of nat. 15α-hydroxy-18-methyl-4-estrene-3,17-dione is combined in 240 ml. of methylene chloride and 64 ml. of ethyl orthoformate with 96 g. of 2,2-dimethyl-1,3-propanediol and 320 mg. of p-toluenesulfonic acid and agitated for 30 minutes under a nitrogen stream at 50° C. The mixture is then diluted with ether, washed with sodium bicarbonate solution and water, dried, and evaporated. The residue is chromatographed on silica gel, there is obtained 37 g. of nat. 15α-hydroxy-3,3-(2',2'-dimethyl-1',3'-propylenedioxy)-18-methyl-5- or -5(10)-estren-17-one in the form of an oil.

c. 37 g. of nat. 15α-hydroxy-3,3-(2',2'-dimethyl-1',3'-propylenedioxy)-18-methyl-5- or -5(10)-estren-17-one is combined in 370 ml. of pyridine under ice cooling with 27.1 ml. of methanesulfochloride and agitated for 3 hours at ice bath temperature. The reaction mixture is then added to ice water, the precipitate is vacuum-filtered, washed thoroughly with water, taken up in methylene chloride, and dried. Yield: 40 g. of nat. 15α-mesyloxy-3,3-(2',2'-dimethyl-1',3'-propylenedioxy)-18-methyl-5- or -5(10)-estren-17-one as an oil.

d. 5.0 g. of trimethyl sulfoxonium iodide is dissolved in 20 ml. of dimethyl sulfoxide, combined with 910 mg. of pulverized sodium hydroxide, and agitated for 60 minutes at room temperature. Under a nitrogen stream, 5.0 g. of nat. 15α-mesyloxy-3,3-(2',2'-dimethyl-1',3'-propylenedioxy)-18-methyl-5- or -5(10)-estren-17-one is then added thereto, and the mixture is agitated for 60 minutes at room temperature. After precipitation in ice water, the thus-formed product is filtered off, washed with water, and taken up in methylene chloride. After evaporation, 2.7 g. of nat. 3,3-(2',2'-dimethyl-1',3'-propylenedioxy)-18-methyl-15β,16β-methylene-5- or -5(10)-estren-17-one is obtained as an oil.

EXAMPLE 2

35 g. of nat. 15α-mesyloxy-3,3-(2',2'-dimethyl-1',3'-propylenedioxy)-18-methyl-5- or -5(10)-estren-17-one is agitated at room temperature in 350 ml. of dimethylformamide with 105 g. of anhydrous sodium acetate for 20 hours. The mixture is then stirred into ice water, the thus-formed precipitate is vacuum-filtered, washed, and taken up in methylene chloride. After evaporation, 28.9 g. of crude nat. 3,3-(2',2'-dimethyl-1',3'-propylenedioxy)-18-methyl-5- or -5(10),15-estradien-17-one is obtained.

EXAMPLE 3 a. 4.0 g. of magnesium filings is reacted with 13.1 ml. of ethyl bromide in 110 ml. of absolute tetrahydrofuran to obtain ethylmagnesium bromide. This solution is added dropwise with ice cooling into 110 ml. of absolute tetrahydrofuran through which acetylene is bubbled. A solution of 12.1 g. of crude nat. 3,3-(2',2'-dimethyl-1',3'-propylenedioxy)-18-methyl-15β,16β-methylene-5- or -5(10)-estren-17-one in 80 ml. of absolute tetrahydrofuran is introduced into this acetylene magnesium bromide solution; the mixture is further agitated for 20 hours at room temperature. Under ice cooling, the excess reagent is then decomposed with saturated ammonium chloride solution. The mixture is thereafter diluted with ether and washed with water. After drying and evaporation, 13 g. of crude nat. 17β-hydroxy-3,3-(2',2'-dimethyl-1',3'-propylenedioxy)-18-methyl-17β-ethynyl-15β,16β-methylene-5- or -5(10)-estrene is obtained in the form of an oil.

b. 13 g. of crude nat. 17β-hydroxy-3,3-(2',2'-dimethyl-1',3'-propylenedioxy)-18-methyl-17α-ethynyl-15β,16β-methylene-5- or -5(10)-estrene is heated under reflux for one hour in 260 ml. of methanol with 26 ml. of water and 13 g. of oxalic acid. The mixture is then stirred into ice water, the precipitate is filtered off, washed, and taken up in methylene chloride. After evaporation, the residue is chromatographed on silica gel, and recrystallization from isopropyl ether/acetone yields 4.8 g. of nat. 17β-hydroxy-18-methyl-17β-ethynyl-15β,16β-methylene-4-estren-3-one, m.p. 141° - 141.5° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of estrene-3,17-dione compounds of Formula I

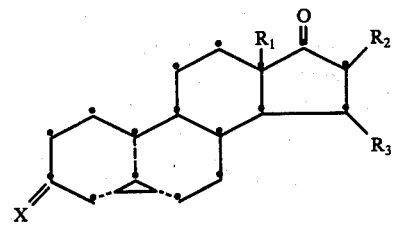

wherein X is keto or ketalized keto;

Δ is a carbon atom linked to the adjacent carbon atoms by a double bond and two single bonds;

$R_1$ is methyl or ethyl; and $R_2$ and $R_3$ collectively are a carbon-to-carbon bond or methylene which comprises a. fermenting an 18-alkyl-4-estrene-3,17-dione of the formula

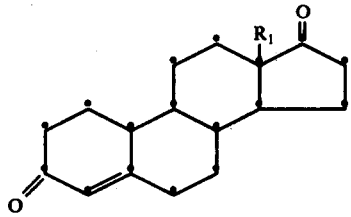

wherein $R_1$ is as above with a fungal culture of the genus Penicillium or Fusarium to produce a 15α-hydroxy steroid of the formula

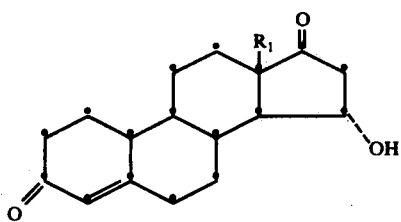

wherein $R_1$ is as above;

b. in either order, ketalizing the 3-keto group of the thus-produced 15α-hydroxy steroid and forming a sulfonic acid ester of the α-hydroxy group thereof; and c. either treating the ketalized and esterified compound (i) with a base to produce a $\Delta^{15}$ steroid of Formula I wherein $R_2$ and $R_3$ collectively are a carbon-to-carbon bond or (ii) with dimethylsulfoxonium methylide to form a 15β,16β-methylene steroid of Formula I wherein $R_2$ and $R_3$ collectively are methylene.

2. The process of claim 1, wherein the fungal culture is Penicillium raistrickii.

3. The process of claim 1, wherein the 15α-hydroxy steroid is first ketalized with an alkanediol of 2–6 carbon atoms or catechol, in the presence of an acidic catalyst, and then acylated with an alkylsulfonyl chloride of 1–6 carbon atoms or an arylsulfonyl chloride of 6–10 carbon atoms, in the presence of a base.

4. The process of claim 1, wherein the 15α-hydroxy steroid is first acylated with an alkylsulfonyl chloride of 1–6 carbon atoms or an arylsulfonyl chloride of 6–10 carbon atoms, in the presence of a base, and then ketalized with an alkanediol of 2–6 carbon atoms or catechol, in the presence of an acidic catalyst.

5. The process of claim 1, wherein the step (c), the ketalized and esterified compound is treated with sodium acetate or potassium acetate in a dipolar aprotic solvent at $-20°$ to $+40°$ C. to form a $\Delta^{15}$-steroid wherein $R_2$ and $R_3$ collectively are a carbon-to-carbon bond.

6. The process of claim 1, wherein $R_1$ is methyl and the fungal culture is Pencillium raistrickii.

7. The process of claim 1, wherein $R_1$ is methyl, the fungal culture is Penicillium raistrickii, the 15α-hydroxy steroid is first ketalized with an alkanediol of 2–6 carbon atoms or a catechol in the presence of an acidic catalyst and then acylated with an alkylsulfonyl chloride of 1–6 carbon atoms or an arylsulfonyl chloride of 6–10 carbon atoms in the presence of a base, and the thus-produced ketalized and esterified compound is treated with sodium acetate or potassium acetate in a dipolar aprotic solvent to form a $\Delta^{15}$-steroid wherein $R_2$ and $R_3$ collectively are a carbon-to-carbon bond.

8. The process of claim 7, wherein said 15α-hydroxy steroid is ketalized with 2,2-dimethyl-1,3-propanediol, acylated with methanesulfonyl chloride and treated with sodium acetate in dimethylsulfoxide.

9. The process of claim 1, wherein $R_1$ is methyl, the fungal culture is Penicillium raistrickii, the 15α-hydroxy steroid is first ketalized with an alkanediol of 2–6 carbon atoms or catechol in the presence of an acidic catalyst and then acylated with an alkylsulfonyl chloride of 1–6 carbon atoms or an arylsulfonyl chloride of 6–10 carbon atoms in the presence of a base, and the thus-produced ketalized and esterified compound is treated with trimethyl sulfoxonium iodide in dimethyl sulfoxide to form a 15β,16β-methylene steroid wherein $R_2$ and $R_3$ collectively are methylene.

10. The process of claim 9, wherein the 15α-hydroxy steroid is first ketalized with 2,2-dimethyl-1,3-propanediol and then acylated with methanesulfonyl chloride in pyridine.

11. The process of claim 1, wherein X in Formula I is keto and the ketal of Step (c) is hydrolyzed with acid.

* * * * *